United States Patent [19]

Harman, III

[11] 4,450,064

[45] May 22, 1984

[54] ELECTROCHEMICAL GAS SENSOR AND METHOD FOR PRODUCING THE SAME

[75] Inventor: John N. Harman, III, Placentia, Calif.

[73] Assignee: Beckman Instruments, Inc., Fullerton, Calif.

[21] Appl. No.: 477,098

[22] Filed: Mar. 21, 1983

[51] Int. Cl.³ .............................................. G01N 27/46
[52] U.S. Cl. ...................................... 204/412; 29/619; 128/635; 204/415
[58] Field of Search ............... 204/412, 415, 416, 418, 204/1 T, 1 Y, 1 P; 128/635; 29/610 R, 619, 621, 825, 854

[56] References Cited

U.S. PATENT DOCUMENTS

| | | | |
|---|---|---|---|
| 3,227,643 | 1/1966 | Okun et al. | 204/415 |
| 3,260,656 | 7/1966 | Ross, Jr. | 204/415 X |
| 3,454,485 | 7/1969 | Hauk et al. | 204/402 |
| 4,076,596 | 2/1978 | Connery et al. | 204/1 T |
| 4,078,981 | 3/1978 | Neti et al. | 204/415 |
| 4,324,257 | 4/1982 | Albarda et al. | 204/412 X |

OTHER PUBLICATIONS

Phelan, et al., "A Maintenance Free Dissolved Oxygen Monitor", American Lab., Jul. 1982, pp. 65–72.

Primary Examiner—G. L. Kaplan
Assistant Examiner—Nam X. Nguyen
Attorney, Agent, or Firm—R. J. Steinmeyer; P. R. Harder; E. C. Jason

[57] ABSTRACT

An improved method for producing an electrode assembly for use in electrochemical gas sensors. A plurality of conductors are attached to one surface of a generally circular electrode blank. These conductors are passed through respective conductor routing holes in an electrically nonconductive mounting member. After the electrode blank is attached to the mounting member, predetermined sections of the electrode blank are cut away to divide the blank into a plurality of electrically isolated regions that are connected to respective conductors. The cut-away sections may then be filled with an electrically nonconductive filling material to provide the electrode assembly with a smooth, flush surface.

14 Claims, 8 Drawing Figures

ELECTROCHEMICAL GAS SENSOR AND METHOD FOR PRODUCING THE SAME

BACKGROUND OF THE INVENTION

The present invention relates to a method for producing electrochemical gas sensors and is directed more particularly to a method for producing electrochemical gas sensors that include a plurality of closely spaced electrodes.

In measuring the concentrations of electrochemically reducible gases such as oxygen, it is a common practice to utilize membrane-type gas sensors. Sensors of the latter type include a gas-permeable membrane that is located at one end of a chamber which is filled with a suitable electrolyte solution, such as an aqueous solution of potassium chloride. Immersed in the electrolyte solution is an anode electrode and a cathode electrode. Of these, the cathode electrode is usually located adjacent to the membrane to maximize its exposure to the gas to be measured. These electrodes are connected to a remote instrument console which applies a polarizing voltage to the electrodes and provides a user-readable indication of the current that flows therebetween.

When oxygen is being measured, for example, oxygen molecules diffuse through the membrane and are reduced to hydroxyl ions in the layer of electrolyte that lies between the membrane and the cathode electrode. As this occurs, a corresponding oxidation reaction occurs at the anode electrode. As the oxygen in this layer of electrolyte is reduced, an oxygen concentration gradient is established between it and the main body of the electrolyte. This concentration gradient, in turn, causes any oxygen that is dissolved in the main body of electrolyte to diffuse toward the cathode electrode. As this dissolved oxygen arrives at the cathode it too is reduced, thereby giving rise to an error in the measured oxygen concentration. The part of the sensor current which is attributable to these diffusing gas molecules represents one component of the residual current of the sensor.

In order to reduce the effect of such residual currents, some gas sensors are provided with guard electrodes which serve to reduce diffusing gas molecules before they arrive at the cathode. One guard electrode of this type is shown in U.S. Pat. No. 3,454,485, issued in the name of Hauk et al., on July 8, 1969.

Guard electrodes have also been used in transcutaneous oxygen sensors. An example of a sensor of the latter type is shown in U.S. Pat. No. 4,324,257, issued in the name of Albarda et al., on Apr. 13, 1982.

While gas sensors having guard electrodes operate satisfactorily, they are expensive to produce. The reason is that guard electrodes and the mounting structures that are used to support them are bulky. As a result, gas sensors that are to include guard electrodes may have to be totally redesigned to accommodate them. This, in turn, may involve the cost of making new injection molds and/or extensive machining.

SUMMARY OF THE INVENTION

In accordance with the present invention, there is provided an improved method for producing a gas sensor having a guard electrode. Generally speaking, the present invention makes use of an electrode mounting member having a plurality of holes, and an electrode blank to which a plurality of conductors have been attached. After passing the conductors through respective holes in the mounting member, the electrode blank is permanently attached to the mounting member. Annular sections of the electrode blank are then cut away to partition the electrode blank into a plurality of electrically isolated regions each of which is connected to a respective conductor. These cutaway sections may then be filled with a suitable electrically nonconductive filling material to produce a smooth, flush surface that includes a plurality of closely spaced electrodes.

In the preferred embodiment, the electrode blank is partitioned into a generally circular inner electrode and a generally annular outer electrode that is concentric therewith. More generally, however, the method of the invention may be used to partition the electrode blank into three or even more electrodes having a variety of different physical configurations. The invention therefore makes possible the fabrication of electrodes which may be used in a variety of different operating modes.

These and other objects of the present invention will become apparent from the following description and drawings in which:

DESCRIPTION OF THE PREFERRED EMBODIMENT

Figure 1:
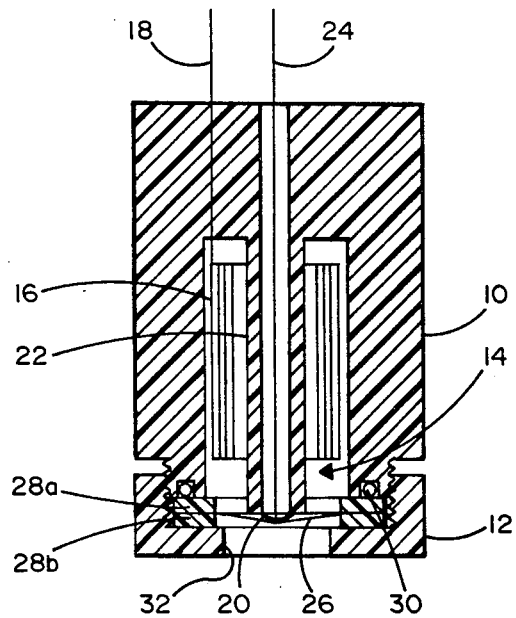
FIG. 1 is a cross-sectional view of a gas sensor of a type that is known in the art.

Referring to FIG. 1 there is shown a simplified cross-sectional view of a gas sensor of a type that is known in the art. This sensor includes upper and lower housing sections 10 and 12, respectively, which may be made of a suitable plastic material such as polyvinyl chloride. Housing sections 10 and 12 enclose a generally cylindrical electrolyte chamber 14 which is filled with a suitable electrolyte solution such as an aqueous solution of potassium chloride. Located within chamber 14 is an anode electrode 16 which comprises a helically wound sheet of a metal such as silver. Electrode 16 may be connected to a suitable polarizing voltage source of a known type (not shown) through a conductor 18. Also located within chamber 14 is a cathode assembly which includes a generally circular cathode electrode 20 that is composed of a noble metal such as gold. The cathode assembly also includes a cathode mounting post 22 and a conductor 24 through which cathode 20 may be connected in closed circuit relationship with the above-mentioned polarizing voltage source.

Closing the lower end of electrolyte chamber 14 is a gas-permeable membrane 26 that typically comprises a thin sheet of polytetrafluoroethylene which is supported in close proximity to cathode 20. This membrane may be mounted in any suitable manner, such as by being sealed between the two halves 28a and 28b of a compression ring assembly which is, in turn, sealed against the lower end of housing 10 by an O-ring 30 when housing section 12 is tightened against housing section 10.

The gas to be measured is supplied to cathode 20 through an opening 32 in lower housing section 12. The component of interest, which may for example be oxygen, diffuses through membrane 26 and into the thin layer of electrolyte that is present between cathode 20 and membrane 26. Once in this thin layer of electrolyte, the oxygen molecules are reduced to hydroxyl ions by electrons received from cathode 20. As this occurs, an equal number of electrons are supplied by the oxidation of silver at anode 16. The current that flows in conductors 18 and 24 as a result of this reaction is therefore a direct measure of the quantity of oxygen that is present. This current is usually measured by means of a remote current measuring instrument (not shown).

Figure 2:
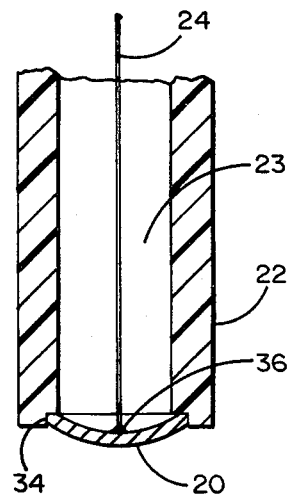
FIG. 2 is an enlarged cross-sectional view of the cathode mounting assembly of the sensor of FIG. 1, FIGS. 3, 7 and 8 are enlarged cross-sectional views of electrode assemblies that have been produced by the practice of the present invention.

Referring to FIG. 2, there is shown an enlarged cross-sectional view of the end of the cathode assembly of FIG. 1. This enlarged view makes clear that cathode 20 rests in a shallow annular recess 34 at the end of mounting member 22. During assembly, cathode electrode 20 is first bonded to wire 24 by a quantity of a suitable solder 36. Then, after applying a quantity of a suitable electrochemically inert cementitious material such as an epoxy resin to recess 34, the cathode and its attached conductor are pushed into an opening 23 through the center of mounting element 22 until cathode 20 comes to rest in recess 34. After this material has cured, internal opening 23 may be filled with a suitable potting compound prior to the assembly of the remainder of the sensor.

Because the operation of the sensor of FIG. 1 consumes oxygen, the layer of electrolyte between cathode 20 and membrane 26 will quickly become depleted in dissolved oxygen. This depletion causes an oxygen concentration gradient to appear between the electrolyte layer and the main body of electrolyte in chamber 14. This gradient, in turn, causes any oxygen that is dissolved in the main body of electrolyte to diffuse toward cathode 20. As this diffusing oxygen enters the electrolyte layer, it too is reduced and thereby gives rise to a current between anode 16 and cathode 20. Since this current bears no relationship to the oxygen concentration outside of membrane 26, it represents an error in the desired oxygen concentration measurement.

As explained in the above-mentioned Hauk et al. patent, the above error may be reduced by providing a guard electrode which surrounds the cathode and consumes any dissolved oxygen which diffuses toward it from chamber 14. This reduction occurs because the current through the guard electrode does not flow through cathode 20 and does not therefore register on the instrument which measures the current between electrodes 16 and 20.

While known types of guard electrodes operate well, they substantially increase the cost of the gas sensors that incorporate them. This is not only because of the cost of the guard electrode and its mounting elements, but also because the gas sensor may have to be entirely redesigned to accommodate these additional elements. Through the use of the present invention, the cost of providing a guard electrode is greatly reduced and the need to change the overall design of the sensor is substantially eliminated. The manner in which this is accomplished is most easily understood with reference to FIGS. 3 and 4.

Figure 3:
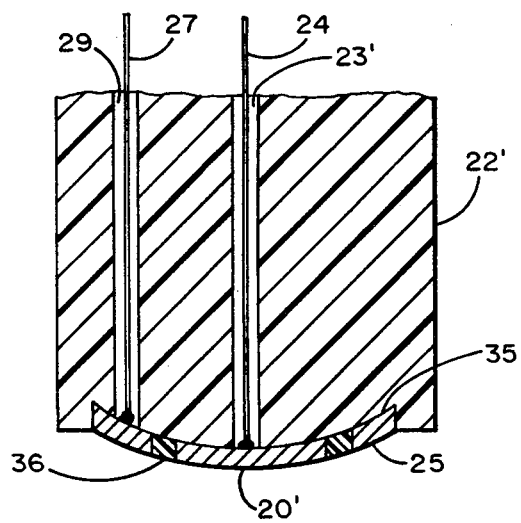
Figure 5:
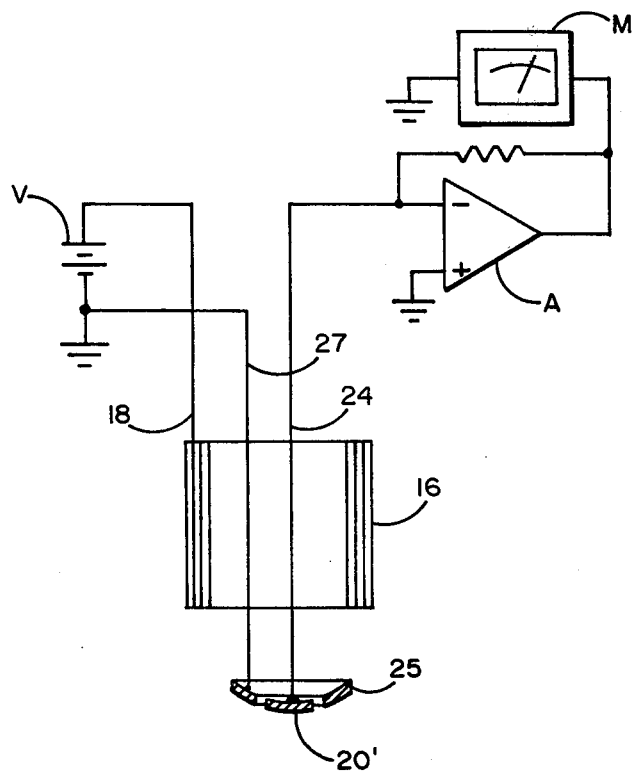
FIGS. 5 and 6 are simplified schematic diagrams which show the electrical connections used with two different gas sensors that are constructed in accordance with the present invention.

Referring to FIG. 3, there is shown an enlarged partial cross-sectional view of an electrode assembly which has been produced in accordance with the present invention. This electrode assembly includes an electrically nonconductive mounting member 22', a generally disc-shaped cathode or measuring electrode 20' and a generally annular shaped guard electrode 25. Electrode 20' is connected to the polarizing voltage source and the current measuring instrument through a conductor 24 which passes through a first, centrally located conductor routing hole 23' in mounting member 22'. Guard electrode 25 is connected to the polarizing voltage source through a conductor 27 which passes through a second, off-center conductor routing hole 29 in mounting member 22'. The connections of these conductors to the polarizing voltage source and the current measuring instrument may be as shown in FIG. 5.

Electrodes 20' and 25 are preferably cemented into a recess 35 which is cut into the end of member 22' and has a shape that matches that of the inner surfaces of electrodes 20' and 25. The open spaces or gaps between electrodes 20' and 25 are preferably filled with a body 36 of a suitable electrochemically inert filling material such as an epoxy resin. This filling material allows the end of the electrode assembly to present a smooth rounded surface to the membrane with which it will operate.

Figure 4:
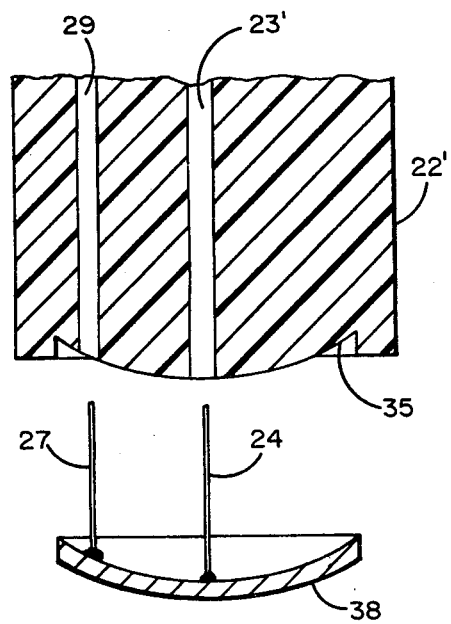
FIG. 4 shows the appearance of the electrode of FIG. 3 prior to the final assembly thereof.

The manner in which the electrode assembly of FIG. 3 is made is most easily understood with reference to FIG. 4, which shows an exploded view of the parts that are used to make it. Included in this exploded view is an electrode blank 38 which comprises a generally disc-shaped piece of metal having a curvature that is substantially the same as that of recess 35. Before electrode blank 38 is attached to mounting member 22', conductors 24 and 27 are soldered to the inner surface thereof at points that allow these conductors to be aligned with conductor routing holes 23' and 29.

After mounting member 22' and electrode blank 38 have been completed, the following steps are performed in completing the electrode assembly of FIG. 3. First, conductors 24 and 27 are passed through respective ones of the conductor routing holes in member 22'. Second, electrode blank 38 is securely attached to member 22'. A suitable electrochemically inert cementitious material such as an epoxy resin may, for example, be placed in recess 35 prior to time that electrode blank 38 is inserted therein. Blank 38 may, however, be attached to member 22' in any manner which will securely hold both the center and edge thereof against member 22'.

After blank 38 has been attached to member 22', a cutting tool such as a lathe is used to cut away an annular section of electrode blank 38 and thereby partition the same into two concentric electrically isolated regions that are connected to conductors 24 and 27, respectively. These two regions correspond to the electrodes labeled 20' and 25 in FIG. 3. The open space or gap between these regions may then, if desired, be filled with a body 36 of the previously mentioned filling material and then trimmed so that the end of the electrode assembly has a smooth flush surface. The gas sensor may then be completed in the usual manner by adding the remaining parts shown in FIG. 1.

In view of the foregoing it will be seen that the machining that is necessary to accommodate the guard electrode is confined to the interior and end of mounting member 22'. Since the interiors and ends of known mounting members also have to be machined, it is apparent that the machining necessary to accommodate the guard elecrtrode does not substantially increase the cost of producing the gas sensor. Moreover, the inclusion of the guard electrode does not require any changes in the molds that are used to produce housing sections 10 and 12. Thus, the practice of the present invention not only produces the desired guard electrode, but does so in a manner that does not significantly change the overall design of the gas sensor or increase the cost of producing the same.

The operation of electrodes 20' and 25 as measuring and guard electrodes will now be discussed with reference to the simplified schematic diagram shown in FIG. 5. As shown in FIG. 5, anode 16 and cathode 20' are connected substantially in series between a source of polarizing voltage V and one input of an operational amplifier A. Since the output current of amplifier A flows through an ammeter M, meter M provides a visual indication of the magnitude of the current flow between the anode and cathode electrodes. Since the latter current is dependent upon the quantity of oxygen which diffuses through membrane 26, the magnitude of the ammeter current can be used as a direct measure of the oxygen concentration in the vicinity of membrane 26.

Unlike measuring electrode 20', guard electrode 25 is connected in series with polarizing voltage source V through a path which does not include the input of amplifier A. As a result, guard electrode 25 is able to consume any dissolved oxygen molecules that appear in the adjacent electrolyte without producing any current in amplifier A. It is therefore able to prevent these oxygen molecules from affecting the flow of current through cathode 20'. Thus, guard electrode 25 prevents meter M from displaying the residual current of the gas sensor.

Figure 6:
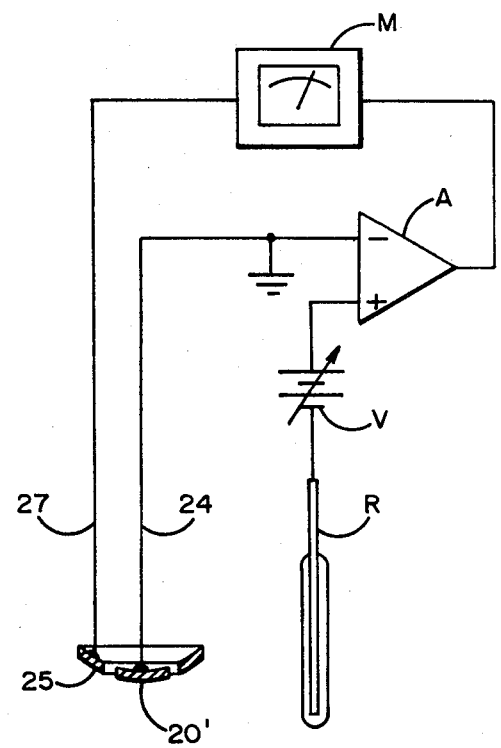

In addition to being usable in the fabrication of gas sensors that include a guard electrode, the present invention may also be used in the fabrication of gas sensors that operate in the potentiostatic mode. A simplified schematic drawing of a gas sensor of the latter type is shown in FIG. 6. In the latter figure the gas sensor includes a cathode electrode 20', an anode electrode 25 and a reference electrode R. Because cathode 20' is connected in closed circuit relationship with reference electrode R, a polarizing voltage source V and the input of amplifier A, the voltage between electrode R and electrode 20' tends to remain substantially constant. As oxygen is reduced at cathode 20', the potential of cathode 20' tends to change, causing amplifier A to produce between electrodes 25 and 20' a current which is just sufficient to force the voltage between the cathode and reference electrodes to return to its original value. Since the magnitude of the latter current is dependent upon the quantity of oxygen that diffuses through membrane 26, the current through meter M can be used as a direct measure of the oxygen concentration in the vicinity of membrane 26. It will therefore be seen that the present invention may be used to fabricate of gas sensors that operate in a variety of different gas detection modes.

Figure 7:
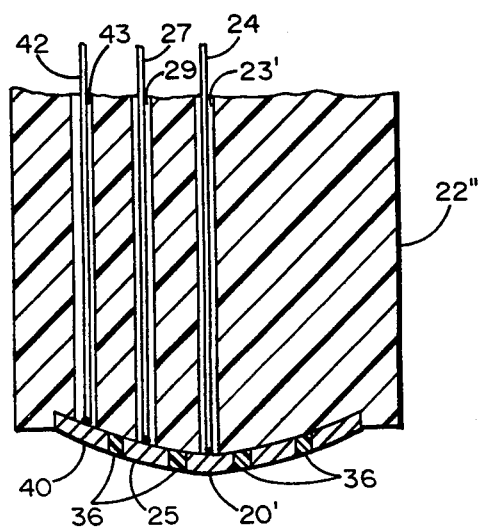

The method of the present invention may also be used in fabricating gas sensors that have more than two electrodes or that have unconventional electrode configurations. Referring to FIG. 7, for example, there is shown an electrode assembly which includes a generally disc-shaped central electrode 20' which is surrounded by two generally annular shaped electrodes 25 and 40. This three-electrode embodiment is produced in generally the same manner as the two-electrode embodiment of FIG. 3. In particular, mounting member 22" is provided with conductor routing holes 23', 29 and 43 through which conductors such as 24, 27 and 42 may be passed. After these conductors are passed through respective holes and the electrode blank is attached to the end of mounting member 22" sections of the electrode blank are cut away to partition the electrode blank into three electrically isolated regions that are connected to respective conductors. The resulting open spaces or gaps may then be filled with the above-mentioned filling material and trimmed to provide a smooth flush surface at the end of the electrode assembly. It will therefore be seen that, provided that the diameter of the electrode blank and mounting element are made large enough, there is no limit to the number of electrodes that may be produced by the practice of the present invention.

Figure 8:
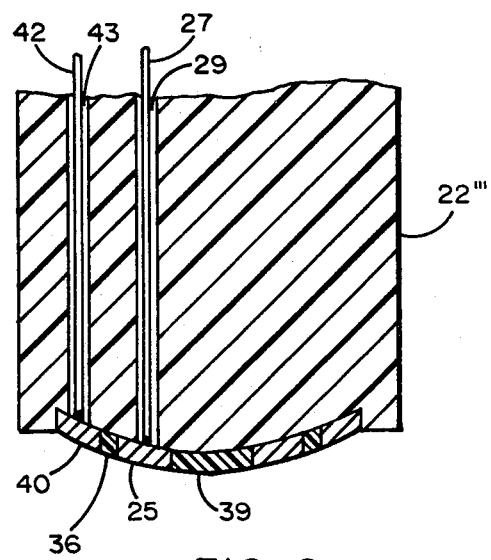

Referring to FIG. 8, there is shown an electrode assembly which is generally similar to that of FIG. 7, except that it does not include a disc-shaped central electrode. An assembly having this configuration may be produced in generally the same manner as the assembly of FIG. 7, except for the additional steps of cutting away the central portion of the electrode blank and filling the resulting opening with a suitable filling material. Alternatively, the electrode assembly of FIG. 8 may be produced by using an electrode blank that has a hole in its center. This central hole may then be filled, as before, or may engage a suitable central projection from mounting member 22'''. Electrode assemblies of the type shown in FIG. 8 are adapted to operate in gas sensors in which the electrodes are preferably relatively narrow and closely spaced. One gas sensor of the latter type is shown and described in U.S. Pat. No. 4,076,596, which issued on Feb. 28, 1978 in the name of Connery et al.

In view of the foregoing, it will be seen that the method of the present invention comprises a simple and inexpensive method for producing electrode assemblies that include a plurality of electrodes which are arranged in any of a variety of different configurations. In addition, because of the way that these electrodes are produced, the present invention lends itself to producing a plurality of electrodes in the same space that had once been occupied by only a single electrode. As a result, the benefits of multi-electrode configurations may be incorporated into existing gas sensors without having to make basic changes in their design.

What is claimed is:

1. An improved method for producing an electrode assembly that includes a plurality of electrodes comprising:
    (a) forming an electrically nonconductive mounting member having a plurality of conductor routing holes,
    (b) forming an electrode blank from an electrically conductive material,
    (c) attaching a plurality of conductors to predetermined points on one surface of the electrode blank,
    (d) passing said conductors through respective ones of said conductor routing holes,
    (e) attaching the electrode blank to the mounting member, and
    (f) cutting away sections of the electrode blank to partition the same into electrically isolated regions that are attached to different respective conductors.

2. The method of claim 1 including the further step of filling in said cutaway sections with an electrically nonconductive filling material.

3. The method of claim 2 including the further step of trimming said filling material to form a smooth surface that is flush with said isolated regions.

4. The method of claim 1 in which the mounting member and the electrode blank are generally circular, and in which the cutting step comprises the cutting away of an annular section of the electrode blank.

5. The method of claim 1 in which the attaching step comprises the cementing of the electrode blank to the mounting member.

6. The method of claim 1 in which the cutting step divides the electrode blank into a plurality of generally circular electrodes which are concentric with one another.

7. An improved electrochemical gas sensor of the type having a gas permeable membrane, a housing defining an electrolyte chamber for receiving an electrolyte solution, and a mounting member for mounting a plurality of electrodes in the electrolyte chamber in the vicinity of the gas permeable membrane, said gas sensor being produced by:
  (a) providing a plurality of conductor routing holes through the mounting member,
  (b) providing an electrode blank having a thickness that is small in relation to its length and width,
  (c) electrically connecting a plurality of conductors to one surface of the electrode blank,
  (d) passing the conductors through respective ones of said routing holes,
  (e) attaching the electrode blank to the mounting member, and
  (f) cutting said blank into electrically isolated regions that are attached to different conductors.

8. The gas sensor of claim 7 in which the electrode blank is generally circular and in which the cutting step cuts away generally annular shaped sections of the electrode blank.

9. The gas sensor of claim 8 produced by the further step of filling in the cutaway sections of the electrode blank with an electrically nonconductive filling material.

10. The gas sensor of claim 9 including the further step of trimming said filling material to form a smooth surface that is flush with said isolated regions.

11. The gas sensor of claim 7 in which the electrode blank is generally circular and in which the cutting step divides the blank into a plurality of electrodes which are concentric with one another.

12. The gas sensor of claim 11 including a disc-shaped inner electrode and at least one generally annular shaped outer electrode.

13. The gas sensor of claim 7 including a plurality of generally annular shaped electrodes.

14. The gas sensor of claim 7 in which the mounting member has a generally cylindrical shape and is located at approximately the center of the electrolyte chamber.

* * * * *